(12) United States Patent
Johansson et al.

(10) Patent No.: US 9,012,037 B2
(45) Date of Patent: Apr. 21, 2015

(54) HOLE TRANSPORT MATERIALS

(75) Inventors: Gary A. Johansson, Hockessin, DE (US); Eric Maurice Smith, Hockessin, DE (US); Daniel David Lecloux, Wilmington, DE (US)

(73) Assignee: EI du Pont de Nemours and Company, Wilmington, DE (US)

( * ) Notice: Subject to any disclaimer, the term of this patent is extended or adjusted under 35 U.S.C. 154(b) by 1182 days.

(21) Appl. No.: 12/129,729

(22) Filed: May 30, 2008

(65) Prior Publication Data

US 2008/0303427 A1 Dec. 11, 2008

Related U.S. Application Data

(60) Provisional application No. 60/941,457, filed on Jun. 1, 2007.

(51) Int. Cl.
*H01L 51/52* (2006.01)
*C07C 211/57* (2006.01)
*C07C 211/54* (2006.01)
*C07C 211/58* (2006.01)
*H01L 51/00* (2006.01)

(52) U.S. Cl.
CPC .............. *C07C 211/58* (2013.01); *C07C 211/54* (2013.01); *H01L 51/001* (2013.01); *H01L 51/0035* (2013.01); *H01L 51/0059* (2013.01); *H01L 51/006* (2013.01)

(58) Field of Classification Search
USPC ........................................................ 428/690
See application file for complete search history.

(56) References Cited

U.S. PATENT DOCUMENTS

| | | | | |
|---|---|---|---|---|
| 5,707,747 A | * | 1/1998 | Tomiyama et al. | ........... 428/457 |
| 2004/0102577 A1 | | 5/2004 | Hsu et al. | |
| 2004/0127637 A1 | | 7/2004 | Hsu et al. | |

(Continued)

FOREIGN PATENT DOCUMENTS

| | | |
|---|---|---|
| EP | 1624500 A | 2/2006 |
| JP | 2001226331 A | 8/2001 |
| JP | 2003238501 A | 8/2003 |

OTHER PUBLICATIONS

Eaton et al. J. Chem. Soc., Faraday Trans. 2, 1973, 69, pp. 1601-1608.*

(Continued)

*Primary Examiner* — Jay L. Yang

(57) ABSTRACT

There is provided a hole transport compound having Formula I or Formula II:

$$(Ar^2)_2N-Ar^1-[T]_n-Ar^1-N(Ar^2)_2 \quad \text{Formula I}$$

$$(Ar^2)_2N-Ar^1-[T]_m-Ar^1-\underset{\underset{Ar^2}{|}}{N}-Ar^1-[T]_n-Ar^1-N(Ar^2)_2 \quad \text{Formula II}$$

$Ar^1$ is the same or different at each occurrence and can be phenylene, naphthylene, or binaphthylene. $Ar^2$ is the same or different at each occurrence and can be phenyl, biphenyl, terphenyl, naphthyl, or binaphthyl. m and n are the same or different and are an integer greater than 0. T is the same or different at each occurrence and is a conjugated moiety including at least one triarylamino group. The T moiety is connected in a non-planar configuration.

12 Claims, 1 Drawing Sheet

(56) References Cited

U.S. PATENT DOCUMENTS

2005/0205860 A1    9/2005  Hsu et al.
2006/0216411 A1*   9/2006  Steudel et al. .................. 427/66

OTHER PUBLICATIONS

CRC Handbook of Chemistry and Physics, 81st Edition, 2000, (Book Not Included).

Y. Wang, Photoconductive Polymers, Kirk-Othmer Encyclopedia of Chemical Technology, 4th Edition, 1996, Vol. 18:837-860.

Gustafsson et al., Flexible Light-Emitting Diodes Made From Soluble Conducting Polymers, Nature, 1992, Vol. 357:477-479.

Kawamura, Hisayuki, Aromatic Oligoamine Derivatives, Their Hole Injection-Transporting Materials, and Their Organic El Devices With Low Driving Voltage, Database CA Chemical Abstract Service, 2003:673842.

Shimamura et al., New Amine Compound for Organic Electroluminescent Device Showing Longer Luminescent Lifetime and Excellent Durability, Chemical Abstracts (English Abstract) XP002492651.

PCT Written Opinion of the International Searching Authority, Application No. WO 2008/150943, PCT/US2008065191, PCT Counterpart of Present Application, Dated Dec. 1, 2009.

* cited by examiner

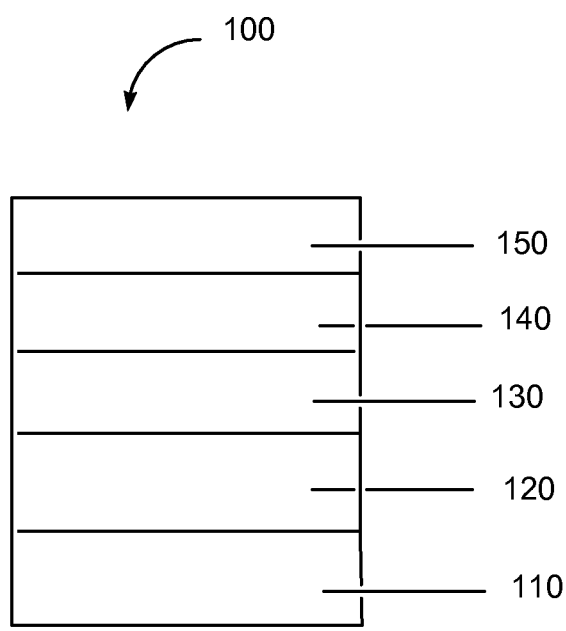

HOLE TRANSPORT MATERIALS

RELATED APPLICATION DATA

This application claims priority under 35 U.S.C. §119(e) from U.S. Provisional Application No. 60/941,457 filed on Jun. 1, 2007, which is incorporated by reference herein in its entirety.

BACKGROUND INFORMATION

1. Field of the Disclosure

The present disclosure relates to novel compounds useful as hole transport materials in making electronic devices. The disclosure further relates to electronic devices having at least one active layer comprising such a hole transport compound.

2. Description of the Related Art

In organic photoactive electronic devices, such as organic light emitting diodes ("OLED"), that make up OLED displays, the organic active layer is sandwiched between two electrical contact layers in an OLED display. In an OLED the organic photoactive layer emits light through the light-transmitting electrical contact layer upon application of a voltage across the electrical contact layers.

It is well known to use organic electroluminescent compounds as the active component in light-emitting diodes. Simple organic molecules, conjugated polymers, and organometallic complexes have been used. Devices that use photoactive materials frequently include one or more charge transport layers, which are positioned between a photoactive (e.g., light-emitting) layer and a contact layer (hole-injecting contact layer). A device can contain two or more contact layers. A hole transport layer can be positioned between the photoactive layer and the hole-injecting contact layer. The hole-injecting contact layer may also be called the anode. An electron transport layer can be positioned between the photoactive layer and the electron-injecting contact layer. The electron-injecting contact layer may also be called the cathode.

There is a continuing need for charge transport materials for use in electronic devices.

SUMMARY

There is provided a hole transport compound having Formula I or Formula II:

$$(Ar^2)_2N-Ar^1\text{-}[T]_n\text{-}Ar^1-N(Ar^2)_2 \quad \text{Formula I}$$

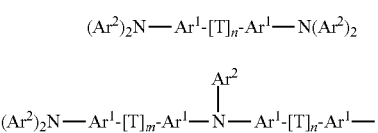

Formula II wherein:
- $Ar^1$ is the same or different at each occurrence and is selected from the group consisting of phenylene, naphthylene, and binaphthylene;
- $Ar^2$ is the same or different at each occurrence and is selected from the group consisting of phenyl, biphenyl, terphenyl, naphthyl, and binaphthyl;
- m and n are the same or different and each is an integer greater than 0; and
- T is the same or different at each occurrence and is a conjugated moiety including at least one triarylamino group, wherein the moiety is connected in a non-planar configuration.

There is also provided a hole transport compound having Formula I or Formula II, as described above, wherein T has Formula III:

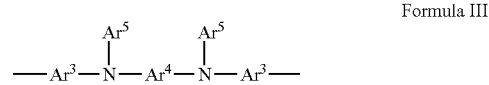

Formula III wherein:
- $Ar^3$ is the same or different at each occurrence and is selected from the group consisting of phenylene, naphthylene, and binaphthylene;
- $Ar^4$ is selected from the group consisting of phenylene, biphenylene, naphthylene, and binaphthylene; and
- $Ar^5$ is the same or different at each occurrence and is selected from the group consisting of phenyl, biphenyl, terphenyl, naphthyl, and binaphthyl.

There is also provided an electronic device having at least one layer comprising the above compound.

The foregoing general description and the following detailed description are exemplary and explanatory only and are not restrictive of the invention, as defined in the appended claims.

BRIEF DESCRIPTION OF THE DRAWINGS

Embodiments are illustrated in the accompanying figures to improve understanding of concepts as presented herein.

FIG. 1 includes an illustration of one example of an organic electronic device.

Skilled artisans appreciate that objects in the figures are illustrated for simplicity and clarity and have not necessarily been drawn to scale. For example, the dimensions of some of the objects in the figures may be exaggerated relative to other objects to help to improve understanding of embodiments.

DETAILED DESCRIPTION

There is provided a hole transport compound having Formula I or Formula II:

Formula I

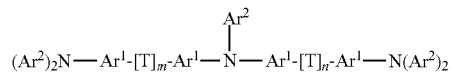

Formula II wherein:
- $Ar^1$ is the same or different at each occurrence and is selected from the group consisting of phenylene, naphthylene, and binaphthylene;
- $Ar^2$ is the same or different at each occurrence and is selected from the group consisting of phenyl, biphenyl, terphenyl, naphthyl, and binaphthyl;
- m and n are the same or different and each is an integer greater than 0; and
- T is the same or different at each occurrence and is a conjugated moiety including at least one triarylamino group, wherein the moiety is connected in a non-planar configuration.

There is also provided a compound having Formula I or Formula II, as described above, wherein T has Formula III:

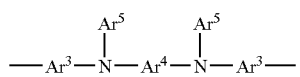

Formula III wherein:
Ar³ is the same or different at each occurrence and is selected from the group consisting of phenylene, naphthylene, and binaphthylene;
Ar⁴ is selected from the group consisting of phenylene, biphenylene, naphthylene, and binaphthylene; and
Ar⁵ is the same or different at each occurrence and is selected from the group consisting of phenyl, biphenyl, terphenyl, naphthyl, and binaphthyl.

There is also provided an electronic device having at least one layer comprising the above compound.

Many aspects and embodiments are described herein and are merely exemplary and not limiting. After reading this specification, skilled artisans appreciate that other aspects and embodiments are possible without departing from the scope of the invention.

Other features and benefits of any one or more of the embodiments will be apparent from the following detailed description, and from the claims. The detailed description first addresses Definitions and Clarification of Terms followed by the Hole Transport Compound, the Electronic Device, and finally Examples.

1. DEFINITIONS AND CLARIFICATION OF TERMS

Before addressing details of embodiments described below, some terms are defined or clarified.

As used herein, the term "alkyl" includes branched and straight-chain saturated aliphatic hydrocarbon groups. Unless otherwise indicated, the term is also intended to include cyclic groups. Examples of alkyl groups include methyl, ethyl, propyl, isopropyl, isobutyl, secbutyl, tertbutyl, pentyl, isopentyl, neopentyl, cyclopentyl, hexyl, cyclohexyl, isohexyl and the like. The term "alkyl" further includes both substituted and unsubstituted hydrocarbon groups. In some embodiments, the alkyl group may be mono-, di- and tri-substituted. One example of a substituted alkyl group is trifluoromethyl. Other substituted alkyl groups are formed from one or more of the substituents described herein. In certain embodiments alkyl groups have 1 to 20 carbon atoms. In other embodiments, the group has 1 to 6 carbon atoms. The term is intended to include heteroalkyl groups. Heteroalkyl groups may have from 1-20 carbon atoms.

The term "aryl" means an aromatic carbocyclic moiety of up to 30 carbon atoms, which may be a single ring (monocyclic) or multiple rings (bicyclic, up to three rings) fused together or linked covalently. Any suitable ring position of the aryl moiety may be covalently linked to the defined chemical structure. Examples of aryl moieties include, but are not limited to, phenyl, 1-naphthyl, 2-naphthyl, dihydronaphthyl, tetrahydronaphthyl, biphenyl. anthryl, phenanthryl, fluorenyl, indanyl, biphenylenyl, acenaphthenyl, acenaphthylenyl, and the like. In some embodiments, aryl groups have 6 to 30 carbon atoms. The term is intended to include heteroaryl groups. Heteroaryl groups may have from 4-30 carbon atoms.

The term "alkoxy" is intended to mean the group —OR, where R is alkyl.

The term "aryloxy" is intended to mean the group —OR, where R is aryl.

The term "binaphthyl" is intended to mean a group having two naphthalene units joined by a single bond. In some embodiments, the binaphthyl group is 1,1-binaphthyl, which is attached at the 3-, 4-, or 5-position; in some embodiments, 1,2-binaphthyl, which is attached at the 3-, 4-, or 5-position on the 1-naphthyl moiety, or the 4- or 5-position on the 2-naphthyl moiety; and in some embodiments, 2,2-binaphthyl, which is attached at the 4- or 5-position. The term "binaphthylene" is intended to mean a binapthyl group having 2 points of attachment.

The term "biphenyl" is intended to mean a group having two phenyl units joined by a single bond. The group can be attached at the 2-, 3-, or 4-position. The term "biphenylene" is intended to mean a biphenyl group having two points of attachment.

Unless otherwise indicated, all groups can be substituted or unsubstituted. An optionally substituted group, such as, but not limited to, alkyl or aryl, may be substituted with one or more substituents which may be the same or different. Suitable substituents include alkyl, aryl, nitro, cyano, —N(R⁷)(R⁸), halo, hydroxy, carboxy, alkenyl, alkynyl, cycloalkyl, heteroaryl, alkoxy, aryloxy, heteroaryloxy, alkoxycarbonyl, perfluoroalkyl, perfluoroalkoxy, arylalkyl, thioalkoxy, —S(O)₂—N(R')(R"), —C(=O)—N(R')(R"), (R')(R")N-alkyl, (R')(R")N-alkoxyalkyl, (R')(R")N-alkylaryloxyalkyl, —S(O)ₛ— aryl (where s=0-2) or —S(O)ₛ-heteroaryl (where s=0-2). Each R' and R" is independently an optionally substituted alkyl, cycloalkyl, or aryl group. R' and R", together with the nitrogen atom to which they are bound, can form a ring system in certain embodiments.

The term "charge transport," when referring to a layer, material, member, or structure is intended to mean such layer, material, member, or structure facilitates migration of such charge through the thickness of such layer, material, member, or structure with relative efficiency and small loss of charge. Hole transport materials facilitate positive charge; electron transport material facilitate negative charge. Although light-emitting materials may also have some charge transport properties, the term "charge transport layer, material, member, or structure" is not intended to include a layer, material, member, or structure whose primary function is light emission.

The term "compound" is intended to mean an electrically uncharged substance made up of molecules that further include atoms, wherein the atoms cannot be separated from their corresponding molecules by physical means without breaking chemical bonds. The term is intended to include oligomers and polymers.

The prefix "hetero" indicates that one or more carbon atoms has been replaced with a different atom. In some embodiments, the heteroatom is O, N, S, or combinations thereof.

The prefix "fluoro" is intended to indicate that one or more hydrogens in a group has been replaced with fluorine.

The term "non-planar configuration" as it refers to Formulae I and II herein, is intended to mean that at least one aromatic portion of the T moiety is oriented in a plane that is different from the plane of the —N(Ar²)₂ moiety.

The term "photoactive" is intended to mean to any material that exhibits electroluminescence or photosensitivity.

The term "crosslinkable group" is intended to mean a group that can lead to crosslinking via thermal treatment or exposure to radiation. In some embodiments, the radiation is UV or visible.

The phrase "adjacent to," when used to refer to layers in a device, does not necessarily mean that one layer is immediately next to another layer. On the other hand, the phrase "adjacent R groups," is used to refer to R groups that are next to each other in a chemical formula (i.e., R groups that are on atoms joined by a bond).

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Group numbers corresponding to columns within the Periodic Table of the elements use the "New Notation" convention as seen in the *CRC Handbook of Chemistry and Physics*, 81st Edition (2000-2001).

Unless otherwise defined, all technical and scientific terms used herein have the same meaning as commonly understood by one of ordinary skill in the art to which this invention belongs. Although methods and materials similar or equivalent to those described herein can be used in the practice or testing of embodiments of the present invention, suitable methods and materials are described below. All publications, patent applications, patents, and other references mentioned herein are incorporated by reference in their entirety, unless a particular passage is cited in case of conflict, the present specification, including definitions, will control. In addition, the materials, methods, and examples are illustrative only and not intended to be limiting.

To the extent not described herein, many details regarding specific materials, processing acts, and circuits are conventional and may be found in textbooks and other sources within the organic light-emitting diode display, photodetector, photovoltaic, and semiconductive member arts.

2. HOLE TRANSPORT COMPOUND

The hole transport compound described herein has Formula I or Formula II:

$$(Ar^2)_2N-Ar^1-[T]_n-Ar^1-N(Ar^2)_2 \quad \text{Formula I}$$

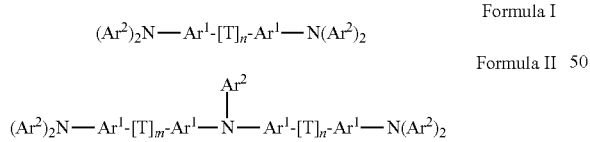

Formula II wherein:
Ar$^1$ is the same or different at each occurrence and is selected from the group consisting of phenylene, naphthylene, and binaphthylene;
Ar$^2$ is the same or different at each occurrence and is selected from the group consisting of phenyl, biphenyl, terphenyl, naphthyl, and binaphthyl;
m and n are the same or different and each is an integer greater than 0; and
T is the same or different at each occurrence and is a conjugated moiety including at least one triarylamino group, wherein the moiety is connected in a non-planar configuration.

In some embodiments, the T moiety has two triarylamino groups.

In some embodiments, T has Formula III:

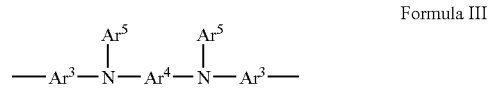

Formula III wherein:
Ar$^3$ is the same or different at each occurrence and is selected from the group consisting of phenylene, naphthylene, and binaphthylene;
Ar$^4$ is selected from the group consisting of phenylene, biphenylene, naphthylene, and binaphthylene; and
Ar$^5$ is the same or different at each occurrence and is selected from the group consisting of phenyl, biphenyl, terphenyl, naphthyl, and binaphthyl.

Any of the aromatic rings in Formulae I-III may be substituted at any position. The substituents may be present to provide steric interactions so that the T moiety is connected in a non-planar configuration. The substituents may be present to improve one or more physical properties of the compound, such as solubility. The substituents may be present to provide crosslinking capability.

In some embodiments, the non-planar configuration is due to the presence of adjacent naphthyl groups. In some embodiment, at least one is a naphthyl group and the adjacent aryl group is also naphthyl. In some embodiments, the compound contains at least one set of adjacent napthyl groups; in some embodiments, two or mores sets of adjacent naphthyl groups. In some embodiments, the naphthyl groups are attached at the 1- and 4-position; in some embodiments the 1- and 5-position.

In some embodiments, the non-planar configuration is due to steric interactions between substituent groups on adjacent aryl groups. In some embodiments, there is at least one set of adjacent aryl groups which each have alkyl or alkoxy substituents. In some embodiments, the adjacent aryl groups are selected from one of the following:

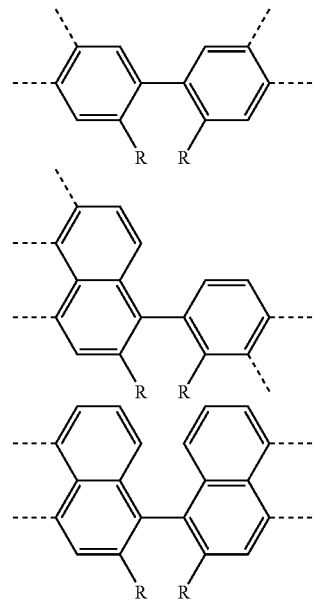

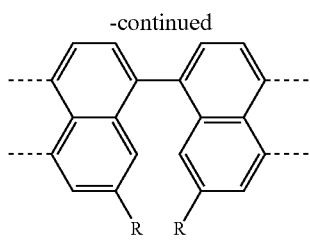

where R represents an alkyl, aryl, alkoxy, or aryloxy group and the dashed line represents a possible point of attachment. In some embodiments, R is a C1-10 alkyl or alkoxy; in some embodiments, a C3-8 branched alkyl or alkoxy.

In some embodiments, there is at least one substituent which includes a crosslinkable group. Examples of crosslinkable groups include, but are not limited to vinyl, acrylate, perfluorovinylether, 1-benzo-3,4-cyclobutane, siloxane, and methyl esters. In one embodiment, the crosslinkable group is vinyl.

In some embodiments, the hole transport compound is selected from Compounds A through H below.

Compound A

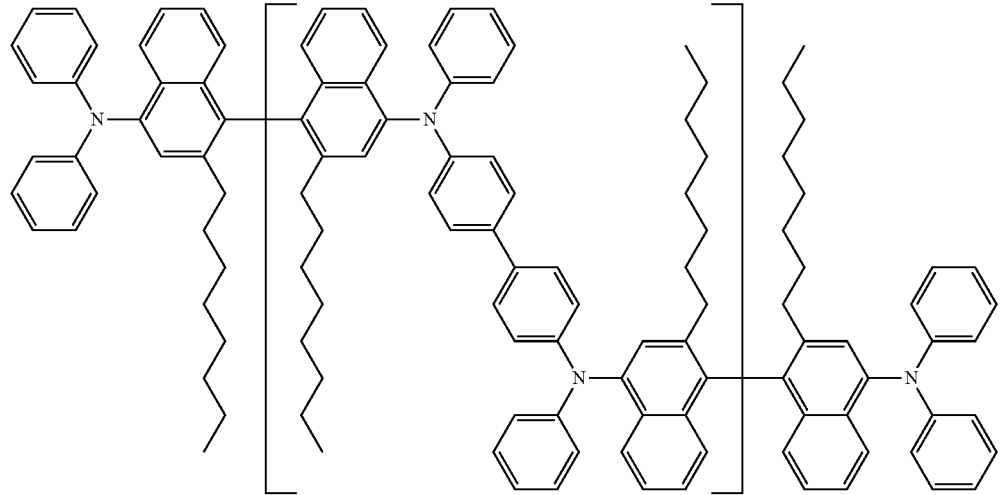

Compound B

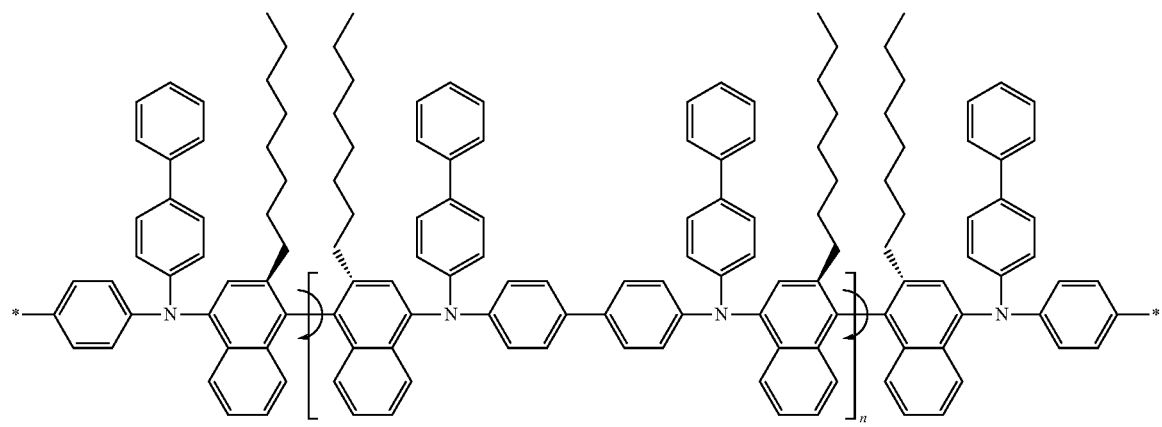

B-1, n = 1
B-2, n = 2
B-3, n = 3

Compound C
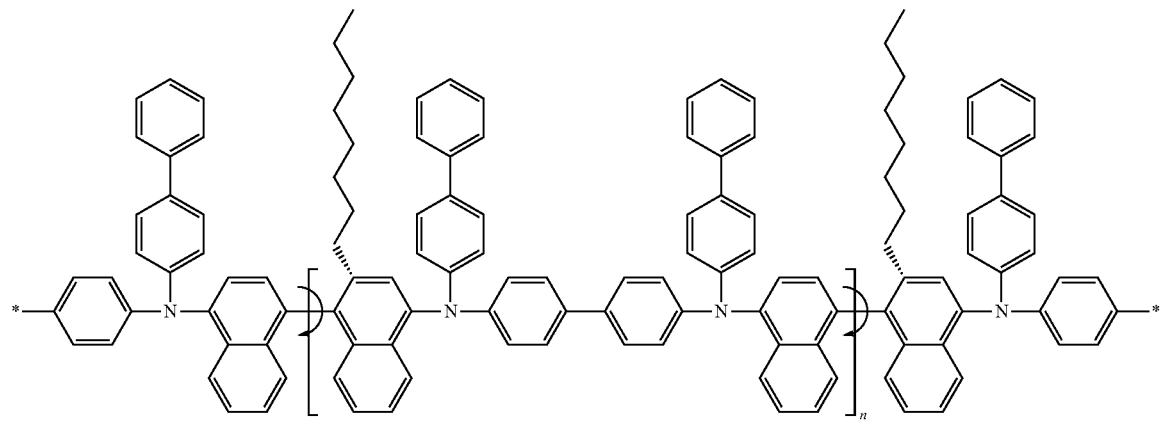
C-1, n = 1
C-2, n = 2
C-3, n = 3
Compound D
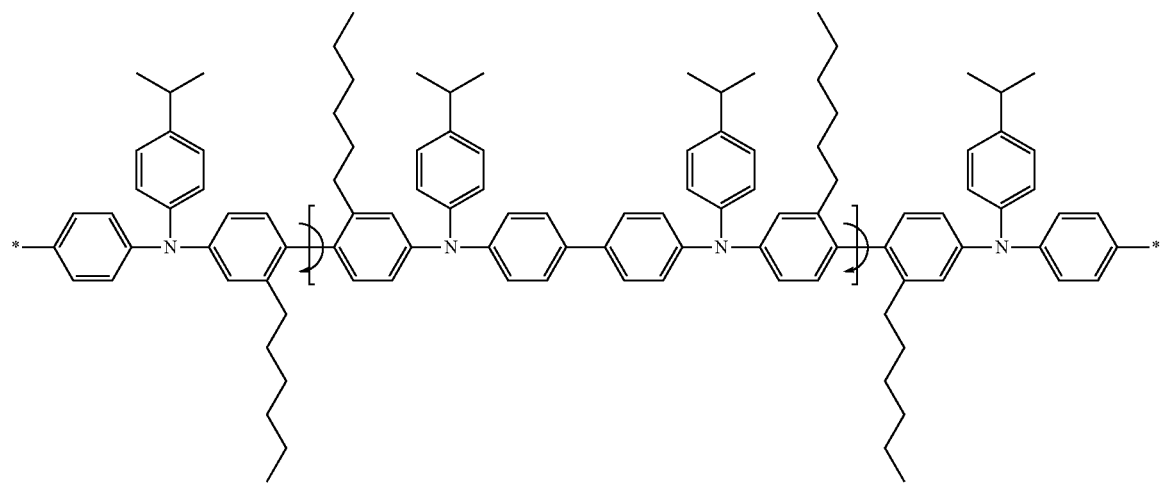
Compound E
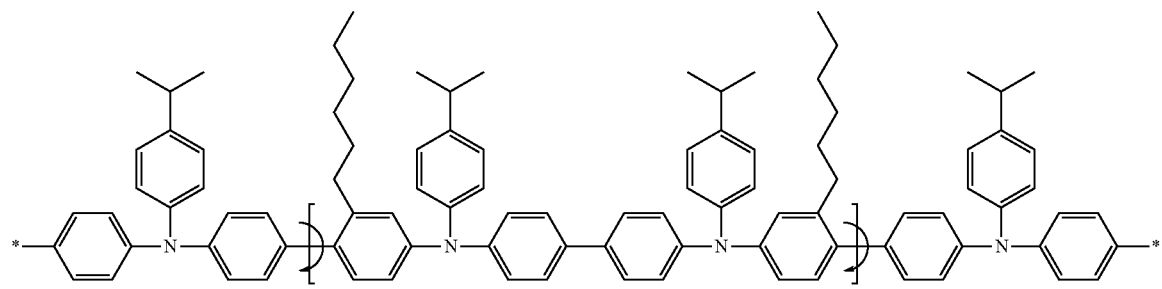

-continued
Compound F
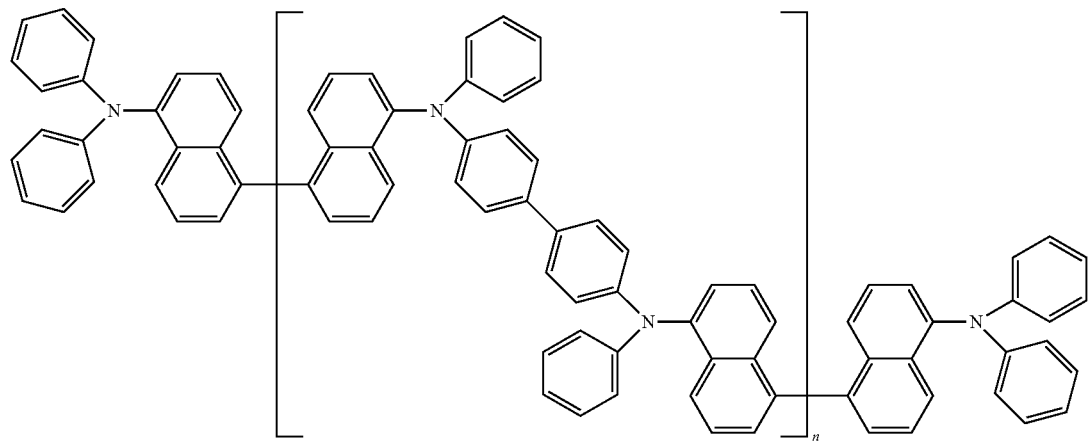
Compound G
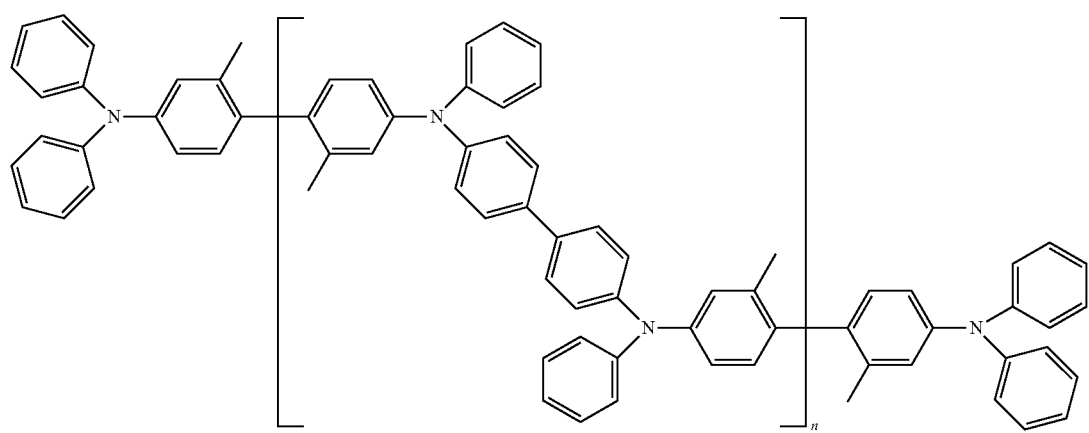
Compound H
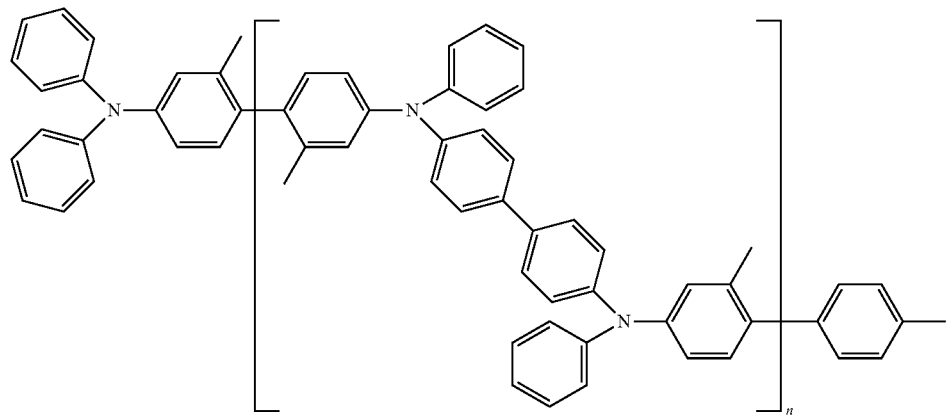

-continued

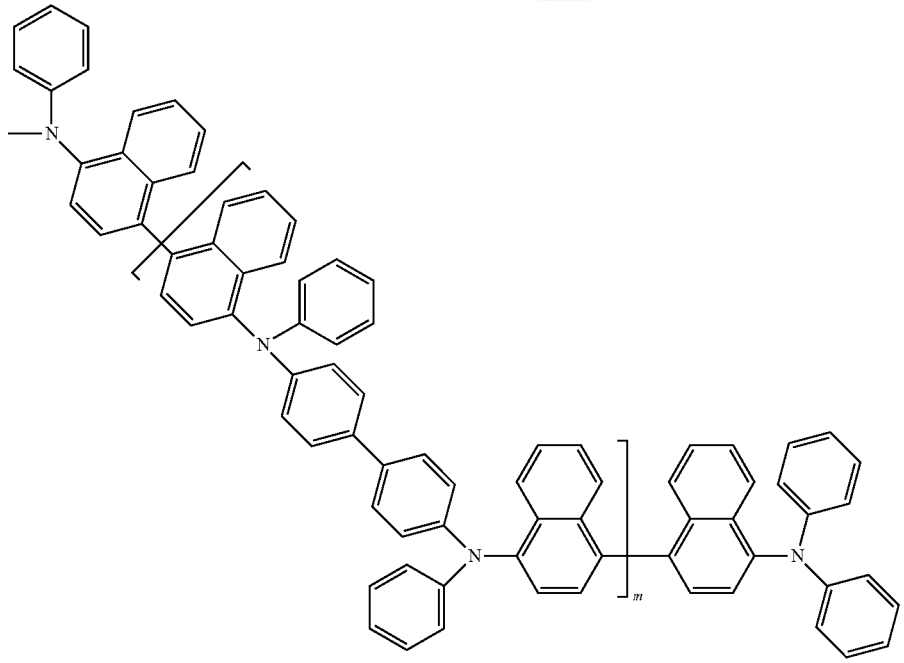

The new compounds can be made using a variety of known techniques, such as Yamamoto coupling. The compounds can be formed into layers using solution processing techniques. The term "layer" is used interchangeably with the term "film" and refers to a coating covering a desired area. The term is not limited by size. The area can be as large as an entire device or as small as a specific functional area such as the actual visual display, or as small as a single sub-pixel. Layers and films can be formed by any conventional deposition technique, including vapor deposition, liquid deposition (continuous and discontinuous techniques), and thermal transfer. Continuous deposition techniques, include but are not limited to, spin coating, gravure coating, curtain coating, dip coating, slot-die coating, spray coating, and continuous nozzle coating. Discontinuous deposition techniques include, but are not limited to, ink jet printing, gravure printing, and screen printing.

The new compounds described herein have hole mobilities and HOMO/LUMO energies similar to efficient small molecule hole transport compounds such as N,N'-diphenyl-N,N'-bis(3-methylphenyl)-[1,1'-biphenyl]-4,4'-diamine (TPD) and N,N'-bis(naphthalen-1-yl)-N,N'-bis-(phenyl)benzidine (α-NPB). Compounds such as TPD and NPD generally must be applied using a vapor deposition technique.

3. ELECTRONIC DEVICES

Organic electronic devices that may benefit from having one or more layers comprising at least one compound as described herein include, but are not limited to, (1) devices that convert electrical energy into radiation (e.g., a light-emitting diode, light emitting diode display, or diode laser), (2) devices that detect signals through electronics processes (e.g., photodetectors, photoconductive cells, photoresistors, photoswitches, phototransistors, phototubes, IR detectors), (3) devices that convert radiation into electrical energy, (e.g., a photovoltaic device or solar cell), and (4) devices that include one or more electronic components that include one or more organic semi-conductor layers (e.g., a transistor or diode). Other uses for the compositions according to the present invention include coating materials for memory storage devices, antistatic films, biosensors, electrochromic devices, solid electrolyte capacitors, energy storage devices such as a rechargeable battery, and electromagnetic shielding applications.

One illustration of an organic electronic device structure is shown in FIG. 1. The device 100 has an anode layer 110 and a cathode layer 150, and a photoactive layer 130 between them. Adjacent to the anode is a layer 120 comprising a charge transport material, for example, a hole transport material. Adjacent to the cathode may be a charge transport layer 140 comprising an electron transport material. As an option, devices may use one or more additional hole injection or hole transport layers (not shown) next to the anode 110 and/or one or more additional electron injection or electron transport layers (not shown) next to the cathode 150.

As used herein, the term "photoactive" refers to a material that emits light when activated by an applied voltage (such as in a light-emitting diode or light-emitting electrochemical cell), or responds to radiant energy and generates a signal with or without an applied bias voltage (such as in a photodetector). In one embodiment, a photoactive layer is an emitter layer.

Depending upon the application of the device 100, the photoactive layer 130 can be a light-emitting layer that is activated by an applied voltage (such as in a light-emitting diode or light-emitting electrochemical cell), a layer of material that responds to radiant energy and generates a signal with or without an applied bias voltage (such as in a photodetector). Examples of photodetectors include photoconductive cells, photoresistors, photoswitches, phototransistors, and phototubes, and photovoltaic cells, as these terms are described in Kirk-Othmer Concise Encyclopedia of Chemical Technology, 4$^{th}$ edition, p. 1537, (1999).

In some embodiments, the hole transport layer 120 comprises at least one new hole transport compound as described herein.

In some embodiments, the device further comprises a buffer layer between the anode and the layer comprising the new polymer. The term "buffer layer" is intended to mean a layer comprising electrically conductive or semiconductive materials and may have one or more functions in an organic electronic device, including but not limited to, planarization of the underlying layer, charge transport and/or charge injection properties, scavenging of impurities such as oxygen or metal ions, and other aspects to facilitate or to improve the performance of the organic electronic device. Buffer materials may be polymers, oligomers, or small molecules, and may be in the form of solutions, dispersions, suspensions, emulsions, colloidal mixtures, or other compositions. The buffer layer can be formed with polymeric materials, such as polyaniline (PANI) or polyethylenedioxythiophene (PEDOT), which are often doped with protonic acids. The protonic acids can be, for example, poly(styrenesulfonic acid), poly(2-acrylamido-2-methyl-1-propanesulfonic acid), and the like. The buffer layer can comprise charge transfer compounds, and the like, such as copper phthalocyanine and the tetrathiafulvalene-tetracyanoquinodimethane system (TTF-TCNQ). In one embodiment, the buffer layer is made from a dispersion of a conducting polymer and a colloid-forming polymeric acid. Such materials have been described in, for example, published U.S. patent applications 2004-0102577, 2004-0127637, and 2005/205860.

In some embodiments, the device further comprises an additional hole transport layer, not shown, between the photoactive layer and the layer 120 comprising the new compound. Examples of other hole transport materials for this additional hole transport layer have been summarized for example, in Kirk Othmer Encyclopedia of Chemical Technology, Fourth Edition, Vol. 18, p. 837 860, 1996, by Y. Wang.

In some embodiments, the photoactive layer comprises at least one photoactive material and at least one new hole transport compound as described herein. The new hole transport compound functions as a host for the photoactive material. In some embodiments, the ratio of host material to photoactive material is in the range of 5:1 to 20:1; in some embodiments, 10:1 to 15:1.

The other layers in the device can be made of any materials which are known to be useful in such layers. The anode 110, is an electrode that is particularly efficient for injecting positive charge carriers. It can be made of, for example materials containing a metal, mixed metal, alloy, metal oxide or mixed-metal oxide, or it can be a conducting polymer, and mixtures thereof. Suitable metals include the Group 11 metals, the metals in Groups 4, 5, and 6, and the Group 8 10 transition metals. If the anode is to be light-transmitting, mixed-metal oxides of Groups 12,13 and 14 metals, such as indium-tin-oxide, are generally used. The anode 110 may also comprise an organic material such as polyaniline as described in "Flexible light-emitting diodes made from soluble conducting polymer," Nature vol. 357, pp 477 479 (11 Jun. 1992). At least one of the anode and cathode should be at least partially transparent to allow the generated light to be observed.

In some embodiments, hole transport layer 120 comprises the new compound described herein. In some embodiments, layer 120 comprises other hole transport materials. Examples of other hole transport materials for layer 120 have been summarized for example, in Kirk Othmer Encyclopedia of Chemical Technology, Fourth Edition, Vol. 18, p. 837 860, 1996, by Y. Wang. Both hole transporting molecules and polymers can be used. Commonly used hole transporting molecules include, but are not limited to: N,N'-diphenyl-N,N'-bis(3-methylphenyl)-[1,1'-biphenyl]-4,4'-diamine (TPD), 1,1-bis[(di-4-tolylamino)phenyl]cyclohexane (TAPC), N,N'-bis(4-methylphenyl)-N,N'-bis(4-ethylphenyl)-[1,1'-(3,3'-dimethyl)biphenyl]-4,4'-diamine (ETPD), tetrakis (3-methylphenyl)-N,N,N',N'-2,5-phenylenediamine (PDA), α-phenyl 4-N,N-diphenylaminostyrene (TPS), p-(diethylamino)benzaldehyde diphenylhydrazone (DEH), triphenylamine (TPA), bis[4 (N,N-diethylamino)-2-methylphenyl](4-methylphenyl)methane (MPMP),1-phenyl-3-[p-(diethylamino)styryl]-5-[p-(diethylamino)phenyl] pyrazoline (PPR or DEASP), 1,2-trans-bis(9H-carbazol-9-yl)cyclobutane (DCZB), N,N,N',N' tetrakis(4-methylphenyl)-(1,1'-biphenyl)-4,4'-diamine (TTB), N,N'-Bis(naphthalen-1-yl)-N,N'-bis-(phenyl)benzidine (α-NPB), and porphyrinic compounds, such as copper phthalocyanine. Commonly used hole transporting polymers include, but are not limited to, polyvinylcarbazole, (phenylmethyl)polysilane, and polyaniline. It is also possible to obtain hole transporting polymers by doping hole transporting molecules such as those mentioned above into polymers such as polystyrene and polycarbonate. Buffer layers and/or hole transport layer can also comprise polymers of thiophene, aniline, or pyrrole with polymeric fluorinated sulfonic acids, as described in published US applications 2004/102577, 2004/127637, and 2005/205860.

Any organic electroluminescent ("EL") material can be used as the photoactive material in layer 130. Such materials include, but are not limited to, one of more compounds of the instant invention, small organic fluorescent compounds, fluorescent and phosphorescent metal complexes, conjugated polymers, and mixtures thereof. Examples of fluorescent compounds include, but are not limited to, pyrene, perylene, rubrene, coumarin, derivatives thereof, and mixtures thereof. Examples of metal complexes include, but are not limited to, metal chelated oxinoid compounds, such as tris(8-hydroxyquinolato)aluminum (Alq3); cyclometalated iridium and platinum electroluminescent compounds, and mixtures thereof. Examples of conjugated polymers include, but are not limited to poly(phenylenevinylenes), polyfluorenes, poly (spirobifluorenes), polythiophenes, poly(p-phenylenes), copolymers thereof, and mixtures thereof. The materials may also be present in admixture with a host material. In some embodiments, the host material is a hole transport material or an electron transport material. In some embodiments, the host is the new compound described herein.

Examples of electron transport materials which can be used in the electron transport layer 140 and/or the optional layer between layer 140 and the cathode include metal chelated oxinoid compounds, such as tris(8-hydroxyquinolato) aluminum (AlQ), bis(2-methyl-8-quinolinolato)(p-phenylphenolato) aluminum (BAlq), tetrakis-(8-hydroxyquinolato)hafnium (HfQ) and tetrakis-(8-hydroxyquinolato)zirconium (ZrQ); and azole compounds such as 2-(4-biphenylyl)-5-(4-t-butylphenyl)-1,3,4-oxadiazole (PBD), 3-(4-biphenylyl)-4-phenyl-5-(4-t-butylphenyl)-1, 2,4-triazole (TAZ), and 1,3,5-tri(phenyl-2-benzimidazole) benzene (TPBI); quinoxaline derivatives such as 2,3-bis(4-fluorophenyl)quinoxaline; phenanthrolines such as 4,7-diphenyl-1,10-phenanthroline (DPA) and 2,9-dimethyl-4,7-diphenyl-1,10-phenanthroline (DDPA); and mixtures thereof.

The cathode 150, is an electrode that is particularly efficient for injecting electrons or negative charge carriers. The cathode can be any metal or nonmetal having a lower work function than the anode. Materials for the cathode can be selected from alkali metals of Group 1 (e.g., Li, Cs), the Group 2 (alkaline earth) metals, the Group 12 metals, including the rare earth elements and lanthanides, and the actinides. Materials such as aluminum, indium, calcium, barium, samarium and magnesium, as well as combinations, can be used. Li-containing organometallic compounds, LiF, and $Li_2O$ can also be deposited between the organic layer and the cathode layer to lower the operating voltage.

The choice of materials for each of the component layers is preferably determined by balancing the goals of providing a device with high device efficiency with device operational lifetime.

The device can be prepared by a variety of techniques, including sequentially depositing the individual layers on a suitable substrate. Substrates such as glass and polymeric films can be used. Conventional vapor deposition techniques can be used, such as thermal evaporation, chemical vapor deposition, and the like. Alternatively, the organic layers can be applied by liquid deposition using suitable solvents. The liquid can be in the form of solutions, dispersions, or emulsions. Typical liquid deposition techniques include, but are not limited to, continuous deposition techniques such as spin coating, gravure coating, curtain coating, dip coating, slot-die coating, spray-coating, and continuous nozzle coating; and discontinuous deposition techniques such as ink jet printing, gravure printing, and screen printing. any conventional coating or printing technique, including but not limited to spin-coating, dip-coating, roll-to-roll techniques, ink jet printing, screen-printing, gravure printing and the like.

The new polymers described herein can be applied by liquid deposition from a liquid composition. The term "liquid composition" is intended to mean a liquid medium in which a material is dissolved to form a solution, a liquid medium in which a material is dispersed to form a dispersion, or a liquid medium in which a material is suspended to form a suspension or an emulsion.

In one embodiment, the different layers have the following range of thicknesses: anode 110, 500-5000 Å, in one embodiment 1000-2000 Å; hole transport layer 120, 50-2000 Å, in one embodiment 200-1000 Å; photoactive layer 130, 10-2000 Å, in one embodiment 100-1000 Å; layer 140, 50-2000 Å, in one embodiment 100-1000 Å; cathode 150, 200-10000 Å, in one embodiment 300-5000 Å. The location of the electron-hole recombination zone in the device, and thus the emission spectrum of the device, can be affected by the relative thickness of each layer. Thus the thickness of the electron-transport layer should be chosen so that the electron-hole recombination zone is in the light-emitting layer. The desired ratio of layer thicknesses will depend on the exact nature of the materials used.

In one embodiment, the device has the following structure, in order: anode, buffer layer, hole transport layer, photoactive layer, electron transport layer, electron injection layer, cathode. In one embodiment, the anode is made of indium tin oxide or indium zinc oxide. In one embodiment, the buffer layer comprises a conducting polymer selected from the group consisting of polythiophenes, polyanilines, polypyrroles, copolymers thereof, and mixtures thereof. In one embodiment, the buffer layer comprises a complex of a conducting polymer and a colloid-forming polymeric acid.

In one embodiment, the hole transport layer comprises the new compound described herein. In one embodiment, the hole transport layer comprises a compound having triarylamine or triarylmethane groups. In one embodiment, the buffer layer comprises a material selected from the group consisting of TPD, MPMP, NPB, CBP, and mixtures thereof, as defined above.

In one embodiment, the photoactive layer comprises an electroluminescent metal complex and a host material. The host can be a charge transport material. In one embodiment, the host is the new compound described herein. In one embodiment, the electroluminescent complex is present in an amount of at least 1% by weight. In one embodiment, the electroluminescent complex is 2-20% by weight. In one embodiment, the electroluminescent complex is 20-50% by weight. In one embodiment, the electroluminescent complex is 50-80% by weight. In one embodiment, the electroluminescent complex is 80-99% by weight. In one embodiment, the metal complex is a cyclometalated complex of iridium, platinum, rhenium, or osmium. In one embodiment, the photoactive layer further comprises a second host material.

In one embodiment, the electron transport layer comprises a metal complex of a hydroxyaryl-N-heterocycle. In one embodiment, the hydroxyaryl-N-heterocycle is unsubstituted or substituted 8-hydroxyquinoline. In one embodiment, the metal is aluminum. In one embodiment, the electron transport layer comprises a material selected from the group consisting of tris(8-hydroxyquinolinato)aluminum, bis(8-hydroxyquinolinato)(4-phenylphenolato)aluminum, tetrakis(8-hydroxyquinolinato)zirconium, tetrakis(8-hydroxyquinolinato)hafnium, and mixtures thereof. In one embodiment, the electron injection layer is LiF or $Li_2O$. In one embodiment, the cathode is Al or Ba/Al. In one embodiment, there is an electron transport layer comprising a material selected from the group consisting of tris(8-hydroxyquinolinato)aluminum, bis(8-hydroxyquinolinato)(4-phenylphenolato)aluminum, tetrakis(8-hydroxyquinolinato)zirconium, tetrakis(8-hydroxyquinolinato)hafnium, and mixtures thereof, and an electron injection layer comprising LiF or $Li_2O$.

In one embodiment, the device is fabricated by liquid deposition of the buffer layer, the hole transport layer, and the photoactive layer, and by vapor deposition of the electron transport layer, the electron injection layer, and the cathode.

The buffer layer can be deposited from any liquid medium in which it is dissolved or dispersed and from which it will form a film. In one embodiment, the liquid medium consists essentially of one or more organic solvents. In one embodiment, the liquid medium consists essentially of water or water and an organic solvent. In one embodiment the organic solvent is selected from the group consisting of alcohols, ketones, cyclic ethers, and polyols. In one embodiment, the organic liquid is selected from dimethylacetamide ("DMAc"), N-methylpyrrolidone ("NMP"), dimethylformamide ("DMF"), ethylene glycol ("EG"), aliphatic alcohols, and mixtures thereof. The buffer material can be present in the liquid medium in an amount from 0.5 to 10 percent by weight. Other weight percentages of buffer material may be used depending upon the liquid medium. The buffer layer can be applied by any continuous or discontinuous liquid deposition technique. In one embodiment, the buffer layer is applied by spin coating. In one embodiment, the buffer layer is applied by ink jet printing. After liquid deposition, the liquid medium can be removed in air, in an inert atmosphere, or by vacuum, at room temperature or with heating. In one embodiment, the layer is heated to a temperature less than 275° C. In one embodiment, the heating temperature is between 100° C. and 275° C. In one embodiment, the heating temperature is between 100° C. and 120° C. In one embodiment, the heating temperature is between 120° C. and 140° C. In one embodiment, the heating temperature is between 140° C. and 160° C. In one embodiment, the heating temperature is between 160° C. and 180° C. In one embodiment, the heating temperature is between 180° C. and 200° C. In one embodiment, the heating temperature is between 200° C. and 220° C. In one embodiment, the heating temperature is between 190° C. and 220° C. In one embodiment, the heating temperature is between 220° C. and 240° C. In one embodiment, the heating temperature is between 240° C. and 260° C. In one embodiment, the heating temperature is between 260° C. and 275° C. The heating time is dependent upon the temperature, and is generally between 5 and 60 minutes. In one embodiment, the final layer thickness is between 5 and 200 nm. In one embodiment, the final layer thickness is between 5 and 40 nm. In one embodiment, the final layer thickness is between 40 and 80 nm. In one embodiment, the final layer thickness is between 80 and 120 nm. In one embodiment, the final layer thickness is between 120 and 160 nm. In one embodiment, the final layer thickness is between 160 and 200 nm.

The hole transport layer can be deposited from any liquid medium in which it is dissolved or dispersed and from which it will form a film. In one embodiment, the liquid medium consists essentially of one or more organic solvents. In one embodiment, the liquid medium consists essentially of water or water and an organic solvent. In one embodiment the organic solvent is an aromatic solvent. In one embodiment, the organic liquid is selected from chloroform, dichloromethane, toluene, anisole, and mixtures thereof. The hole transport material can be present in the liquid medium in a concentration of 0.2 to 2 percent by weight. Other weight percentages of hole transport material may be used depending upon the liquid medium. The hole transport layer can be applied by any continuous or discontinuous liquid deposition technique. In one embodiment, the hole transport layer is applied by spin coating. In one embodiment, the hole transport layer is applied by ink jet printing. After liquid deposition, the liquid medium can be removed in air, in an inert atmosphere, or by vacuum, at room temperature or with heating. In one embodiment, the layer is heated to a temperature of 300° C. or less. In one embodiment, the heating temperature is between 170° C. and 275° C. In one embodiment, the heating temperature is between 170° C. and 200° C. In one embodiment, the heating temperature is between 190° C. and 220° C. In one embodiment, the heating temperature is between 210° C. and 240° C. In one embodiment, the heating temperature is between 230° C. and 270° C. The heating time is dependent upon the temperature, and is generally between 5 and 60 minutes. In one embodiment, the final layer thickness is between 5 and 50 nm. In one embodiment, the final layer thickness is between 5 and 15 nm. In one embodiment, the final layer thickness is between 15 and 25 nm. In one embodiment, the final layer thickness is between 25 and 35 nm. In one embodiment, the final layer thickness is between 35 and 50 nm.

The photoactive layer can be deposited from any liquid medium in which it is dissolved or dispersed and from which it will form a film. In one embodiment, the liquid medium consists essentially of one or more organic solvents. In one embodiment, the liquid medium consists essentially of water or water and an organic solvent. In one embodiment the organic solvent is an aromatic solvent. In one embodiment, the organic liquid is selected from chloroform, dichloromethane, toluene, anisole, and mixtures thereof. The photoactive material can be present in the liquid medium in a concentration of 0.2 to 2 percent by weight. Other weight percentages of photoactive material may be used depending upon the liquid medium. The photoactive layer can be applied by any continuous or discontinuous liquid deposition technique. In one embodiment, the photoactive layer is applied by spin coating. In one embodiment, the photoactive layer is applied by ink jet printing. After liquid deposition, the liquid medium can be removed in air, in an inert atmosphere, or by vacuum, at room temperature or with heating. In one embodiment, the deposited layer is heated to a temperature that is less than the Tg of the material having the lowest Tg. In one embodiment, the heating temperature is at least 10° C. less than the lowest Tg. In one embodiment, the heating temperature is at least 20° C. less than the lowest Tg. In one embodiment, the heating temperature is at least 30° C. less than the lowest Tg. In one embodiment, the heating temperature is between 50° C. and 150° C. In one embodiment, the heating temperature is between 50° C. and 75° C. In one embodiment, the heating temperature is between 75° C. and 100° C. In one embodiment, the heating temperature is between 100° C. and 125° C. In one embodiment, the heating temperature is between 125° C. and 150° C. The heating time is dependent upon the temperature, and is generally between 5 and 60 minutes. In one embodiment, the final layer thickness is between 25 and 100 nm. In one embodiment, the final layer thickness is between 25 and 40 nm. In one embodiment, the final layer thickness is between 40 and 65 nm. In one embodiment, the final layer thickness is between 65 and 80 nm. In one embodiment, the final layer thickness is between 80 and 100 nm.

The electron transport layer can be deposited by any vapor deposition method. In one embodiment, it is deposited by thermal evaporation under vacuum. In one embodiment, the final layer thickness is between 1 and 100 nm. In one embodiment, the final layer thickness is between 1 and 15 nm. In one embodiment, the final layer thickness is between 15 and 30 nm. In one embodiment, the final layer thickness is between 30 and 45 nm. In one embodiment, the final layer thickness is between 45 and 60 nm. In one embodiment, the final layer thickness is between 60 and 75 nm. In one embodiment, the final layer thickness is between 75 and 90 nm. In one embodiment, the final layer thickness is between 90 and 100 nm.

The electron injection layer can be deposited by any vapor deposition method. In one embodiment, it is deposited by thermal evaporation under vacuum. In one embodiment, the vacuum is less than $10^{-6}$ torr. In one embodiment, the vacuum is less than $10^{-7}$ torr. In one embodiment, the vacuum is less than $10^{-8}$ torr. In one embodiment, the material is heated to a temperature in the range of 100° C. to 400° C.; 150° C. to 350° C. preferably. All vapor deposition rates given herein are in units of Angstroms per second. In one embodiment, the material is deposited at a rate of 0.5 to 10 Å /sec. In one embodiment, the material is deposited at a rate of 0.5 to 1 Å /sec. In one embodiment, the material is deposited at a rate of 1 to 2 Å /sec. In one embodiment, the material is deposited at a rate of 2 to 3 Å /sec. In one embodiment, the material is deposited at a rate of 3 to 4 Å /sec. In one embodiment, the material is deposited at a rate of 4 to 5 Å /sec. In one embodiment, the material is deposited at a rate of 5 to 6 Å /sec. In one embodiment, the material is deposited at a rate of 6 to 7 Å /sec. In one embodiment, the material is deposited at a rate of 7 to 8 Å /sec. In one embodiment, the material is deposited at a rate of 8 to 9 Å /sec. In one embodiment, the material is deposited at a rate of 9 to 10 Å /sec. In one embodiment, the final layer thickness is between 0.1 and 3 nm. In one embodiment, the final layer thickness is between 0.1 and 1 nm. In one embodiment, the final layer thickness is between 1 and 2 nm. In one embodiment, the final layer thickness is between 2 and 3 nm.

The cathode can be deposited by any vapor deposition method. In one embodiment, it is deposited by thermal evaporation under vacuum. In one embodiment, the vacuum is less than $10^{-6}$ torr. In one embodiment, the vacuum is less than $10^{-7}$ torr. In one embodiment, the vacuum is less than $10^{-8}$ torr. In one embodiment, the material is heated to a temperature in the range of 100° C. to 400° C.; 150° C. to 350° C. preferably. In one embodiment, the material is deposited at a rate of 0.5 to 10 Å/sec. In one embodiment, the material is deposited at a rate of 0.5 to 1 Å/sec. In one embodiment, the material is deposited at a rate of 1 to 2 Å/sec. In one embodiment, the material is deposited at a rate of 2 to 3 Å/sec. In one embodiment, the material is deposited at a rate of 3 to 4 Å/sec. In one embodiment, the material is deposited at a rate of 4 to 5 Å/sec. In one embodiment, the material is deposited at a rate of 5 to 6 Å/sec. In one embodiment, the material is deposited at a rate of 6 to 7 Å/sec. In one embodiment, the material is deposited at a rate of 7 to 8 Å/sec. In one embodiment, the material is deposited at a rate of 8 to 9 Å/sec. In one embodiment, the material is deposited at a rate of 9 to 10 Å/sec. In one embodiment, the final layer thickness is between 10 and 10000 nm. In one embodiment, the final layer thickness is between 10 and 1000 nm. In one embodiment, the final layer thickness is between 10 and 50 nm. In one embodiment, the final layer thickness is between 50 and 100 nm. In one embodiment, the final layer thickness is between 100 and 200 nm. In one embodiment, the final layer thickness is between 200 and 300 nm. In one embodiment, the final layer thickness is between 300 and 400 nm. In one embodiment, the final layer thickness is between 400 and 500 nm. In one embodiment, the final layer thickness is between 500 and 600 nm. In one embodiment, the final layer thickness is between 600 and 700 nm. In one embodiment, the final layer thickness is between 700 and 800 nm. In one embodiment, the final layer thickness is between 800 and 900 nm. In one embodiment, the final layer thickness is between 900 and 1000 nm. In one embodiment, the final layer thickness is between 1000 and 2000 nm. In one embodiment, the final layer thickness is between 2000 and 3000 nm. In one embodiment, the final layer thickness is between 3000 and 4000 nm. In one embodiment, the final layer thickness is between 4000 and 5000 nm. In one embodiment, the final layer thickness is between 5000 and 6000 nm. In one embodiment, the final layer thickness is between 6000 and 7000 nm. In one embodiment, the final layer thickness is between 7000 and 8000 nm. In one embodiment, the final layer thickness is between 8000 and 9000 nm. In one embodiment, the final layer thickness is between 9000 and 10000 nm.

In one embodiment, the device is fabricated by vapor deposition of the buffer layer, the hole transport layer, and the photoactive layer, the electron transport layer, the electron injection layer, and the cathode.

In one embodiment, the buffer layer is applied by vapor deposition. In one embodiment, it is deposited by thermal evaporation under vacuum. In one embodiment, the vacuum is less than $10^{-6}$ torr. In one embodiment, the vacuum is less than $10^{-7}$ torr. In one embodiment, the vacuum is less than $10^{-8}$ torr. In one embodiment, the material is heated to a temperature in the range of 100° C. to 400° C.; 150° C. to 350° C. preferably. In one embodiment, the material is deposited at a rate of 0.5 to 10 Å/sec. In one embodiment, the material is deposited at a rate of 0.5 to 1 Å/sec. In one embodiment, the material is deposited at a rate of 1 to 2 Å/sec. In one embodiment, the material is deposited at a rate of 2 to 3 Å/sec. In one embodiment, the material is deposited at a rate of 3 to 4 Å/sec. In one embodiment, the material is deposited at a rate of 4 to 5 Å/sec. In one embodiment, the material is deposited at a rate of 5 to 6 Å/sec. In one embodiment, the material is deposited at a rate of 6 to 7 Å/sec. In one embodiment, the material is deposited at a rate of 7 to 8 Å/sec. In one embodiment, the material is deposited at a rate of 8 to 9 Å/sec. In one embodiment, the material is deposited at a rate of 9 to 10 Å/sec. In one embodiment, the final layer thickness is between 5 and 200 nm. In one embodiment, the final layer thickness is between 5 and 30 nm. In one embodiment, the final layer thickness is between 30 and 60 nm. In one embodiment, the final layer thickness is between 60 and 90 nm. In one embodiment, the final layer thickness is between 90 and 120 nm. In one embodiment, the final layer thickness is between 120 and 150 nm. In one embodiment, the final layer thickness is between 150 and 280 nm. In one embodiment, the final layer thickness is between 180 and 200 nm.

In one embodiment, the hole transport layer is applied by vapor deposition. In one embodiment, it is deposited by thermal evaporation under vacuum. In one embodiment, the vacuum is less than $10^{-6}$ torr. In one embodiment, the vacuum is less than $10^{-7}$ torr. In one embodiment, the vacuum is less than $10^{-8}$ torr. In one embodiment, the material is heated to a temperature in the range of 100° C. to 400° C.; 150° C. to 350° C. preferably. In one embodiment, the material is deposited at a rate of 0.5 to 10 Å/sec. In one embodiment, the material is deposited at a rate of 0.5 to 1 Å/sec. In one embodiment, the material is deposited at a rate of 1 to 2 Å/sec. In one embodiment, the material is deposited at a rate of 2 to 3 Å/sec. In one embodiment, the material is deposited at a rate of 3 to 4 Å/sec. In one embodiment, the material is deposited at a rate of 4 to 5 Å/sec. In one embodiment, the material is deposited at a rate of 5 to 6 Å/sec. In one embodiment, the material is deposited at a rate of 6 to 7 Å/sec. In one embodiment, the material is deposited at a rate of 7 to 8 Å/sec. In one embodiment, the material is deposited at a rate of 8 to 9 Å/sec. In one embodiment, the material is deposited at a rate of 9 to 10 Å/sec. In one embodiment, the final layer thickness is between 5 and 200 nm. In one embodiment, the final layer thickness is between 5 and 30 nm. In one embodiment, the final layer thickness is between 30 and 60 nm. In one embodiment, the final layer thickness is between 60 and 90 nm. In one embodiment, the final layer thickness is between 90 and 120 nm. In one embodiment, the final layer thickness is between 120 and 150 nm. In one embodiment, the final layer thickness is between 150 and 280 nm. In one embodiment, the final layer thickness is between 180 and 200 nm.

In one embodiment, the photoactive layer is applied by vapor deposition. In one embodiment, it is deposited by thermal evaporation under vacuum. In one embodiment, the photoactive layer consists essentially of a single electroluminescent compound, which is deposited by thermal evaporation under vacuum. In one embodiment, the vacuum is less than $10^{-6}$ torr. In one embodiment, the vacuum is less than $10^{-7}$ torr. In one embodiment, the vacuum is less than $10^{-8}$ torr. In one embodiment, the material is heated to a temperature in the range of 100° C. to 400° C.; 150° C. to 350° C. preferably. In one embodiment, the material is deposited at a rate of 0.5 to 10 Å/sec. In one embodiment, the material is deposited at a rate of 0.5 to 1 Å/sec. In one embodiment, the material is deposited at a rate of 1 to 2 Å/sec. In one embodiment, the material is deposited at a rate of 2 to 3 Å/sec. In one embodiment, the material is deposited at a rate of 3 to 4 Å/sec. In one embodiment, the material is deposited at a rate of 4 to 5 Å/sec. In one embodiment, the material is deposited at a rate of 5 to 6 Å/sec. In one embodiment, the material is deposited at a rate of 6 to 7 Å/sec. In one embodiment, the material is deposited at a rate of 7 to 8 Å/sec. In one embodiment, the material is deposited at a rate of 8 to 9 Å/sec. In one embodiment, the material is deposited at a rate of 9 to 10 Å/sec. In one embodiment, the final layer thickness is between 5 and 200 nm. In one embodiment, the final layer thickness is between 5 and 30 nm. In one embodiment, the final layer thickness is between 30 and 60 nm. In one embodiment, the final layer thickness is between 60 and 90 nm. In one embodiment, the final layer thickness is between 90 and 120 nm. In one embodiment, the final layer thickness is between 120 and 150 nm. In one embodiment, the final layer thickness is between 150 and 280 nm. In one embodiment, the final layer thickness is between 180 and 200 nm.

In one embodiment, the photoactive layer comprises two electroluminescent materials, each of which is applied by thermal evaporation under vacuum. Any of the above listed vacuum conditions and temperatures can be used. Any of the above listed deposition rates can be used. The relative deposition rates can be from 50:1 to 1:50. In one embodiment, the relative deposition rates are from 1:1 to 1:3. In one embodiment, the relative deposition rates are from 1:3 to 1:5. In one embodiment, the relative deposition rates are from 1:5 to 1:8. In one embodiment, the relative deposition rates are from 1:8 to 1:10. In one embodiment, the relative deposition rates are from 1:10 to 1:20. In one embodiment, the relative deposition rates are from 1:20 to 1:30. In one embodiment, the relative deposition rates are from 1:30 to 1:50. The total thickness of the layer can be the same as that described above for a single-component photoactive layer.

In one embodiment, the photoactive layer comprises one electroluminescent material and at least one host material, each of which is applied by thermal evaporation under vacuum. Any of the above listed vacuum conditions and temperatures can be used. Any of the above listed deposition rates can be used. The relative deposition rate of electroluminescent material to host can be from 1:1 to 1:99. In one embodiment, the relative deposition rates are from 1:1 to 1:3. In one embodiment, the relative deposition rates are from 1:3 to 1:5. In one embodiment, the relative deposition rates are from 1:5 to 1:8. In one embodiment, the relative deposition rates are from 1:8 to 1:10. In one embodiment, the relative deposition rates are from 1:10 to 1:20. In one embodiment, the relative deposition rates are from 1:20 to 1:30. In one embodiment, the relative deposition rates are from 1:30 to 1:40. In one embodiment, the relative deposition rates are from 1:40 to 1:50. In one embodiment, the relative deposition rates are from 1:50 to 1:60. In one embodiment, the relative deposition rates are from 1:60 to 1:70. In one embodiment, the relative deposition rates are from 1:70 to 1:80. In one embodiment, the relative deposition rates are from 1:80 to 1:90. In one embodiment, the relative deposition rates are from 1:90 to 1:99. The total thickness of the layer can be the same as that described above for a single-component photoactive layer.

In one embodiment, the electron transport layer is applied by vapor deposition. In one embodiment, it is deposited by thermal evaporation under vacuum. In one embodiment, the vacuum is less than $10^{-6}$ torr. In one embodiment, the vacuum is less than $10^{-7}$ torr. In one embodiment, the vacuum is less than $10^{-8}$ torr. In one embodiment, the material is heated to a temperature in the range of 100° C. to 400° C.; 150° C. to 350° C. preferably. In one embodiment, the material is deposited at a rate of 0.5 to 10 Å/sec. In one embodiment, the material is deposited at a rate of 0.5 to 1 Å/sec. In one embodiment, the material is deposited at a rate of 1 to 2 Å/sec. In one embodiment, the material is deposited at a rate of 2 to 3 Å/sec. In one embodiment, the material is deposited at a rate of 3 to 4 Å/sec. In one embodiment, the material is deposited at a rate of 4 to 5 Å/sec. In one embodiment, the material is deposited at a rate of 5 to 6 Å/sec. In one embodiment, the material is deposited at a rate of 6 to 7 Å/sec. In one embodiment, the material is deposited at a rate of 7 to 8 Å/sec. In one embodiment, the material is deposited at a rate of 8 to 9 Å/sec. In one embodiment, the material is deposited at a rate of 9 to 10 Å/sec. In one embodiment, the final layer thickness is between 5 and 200 nm. In one embodiment, the final layer thickness is between 5 and 30 nm. In one embodiment, the final layer thickness is between 30 and 60 nm. In one embodiment, the final layer thickness is between 60 and 90 nm. In one embodiment, the final layer thickness is between 90 and 120 nm. In one embodiment, the final layer thickness is between 120 and 150 nm. In one embodiment, the final layer thickness is between 150 and 280 nm. In one embodiment, the final layer thickness is between 180 and 200 nm.

In one embodiment, the electron injection layer is applied by vapor deposition, as described above.

In one embodiment, the cathode is applied by vapor deposition, as describe above.

In one embodiment, the device is fabricated by vapor deposition of some of the organic layers, and liquid deposition of some of the organic layers. In one embodiment, the device is fabricated by liquid deposition of the buffer layer, and vapor deposition of all of the other layers Although methods and materials similar or equivalent to those described herein can be used in the practice or testing of the present invention, suitable methods and materials are described below. In addition, the materials, methods, and examples are illustrative only and not intended to be limiting. All publications, patent applications, patents, and other references mentioned herein are incorporated by reference in their entirety.

EXAMPLES

The concepts described herein will be further described in the following examples, which do not limit the scope of the invention described in the claims.

Note that not all of the activities described above in the general description or the examples are required, that a portion of a specific activity may not be required, and that one or more further activities may be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

It is to be appreciated that certain features are, for clarity, described herein in the context of separate embodiments, may also be provided in combination in a single embodiment. Conversely, various features that are, for brevity, described in the context of a single embodiment, may also be provided separately or in any subcombination. Further, reference to values stated in ranges include each and every value within that range.

What is claimed is:

1. A liquid processable hole transport compound having Formula I or Formula II:

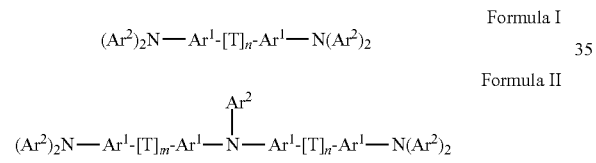

wherein:
Ar¹ is the same or different at each occurrence and is selected from the group consisting of phenylene, naphthylene, and binaphthylene;
Ar² is the same or different at each occurrence and is selected from the group consisting of phenyl, biphenyl, terphenyl, naphthyl, and binaphthyl;
m and n are the same or different and each is an integer greater than 0; and
T is the same or different at each occurrence and is a conjugated moiety including at least one triarylamino group, wherein the moiety is connected in a non-planar configuration;
wherein the compound comprises at least one set of adjacent aryl groups selected from one of the following:

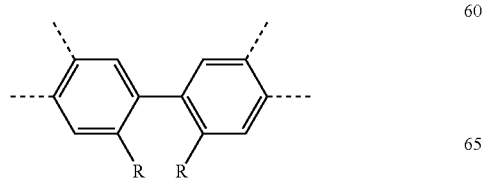

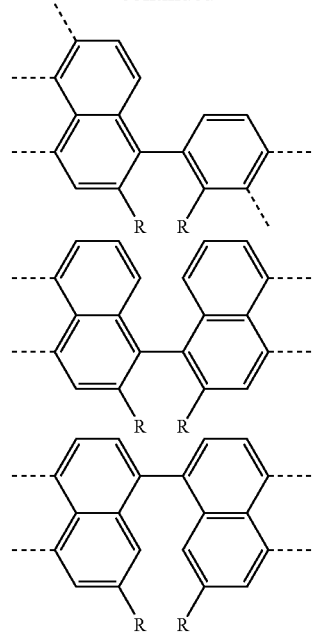

where R represents an alkyl, aryl, alkoxy, or aryloxy group and the dashed line represents a possible point of attachment,
further comprising at least two sets of adjacent naphthyl groups.

2. A liquid processable hole transport compound having Formula I or Formula II:

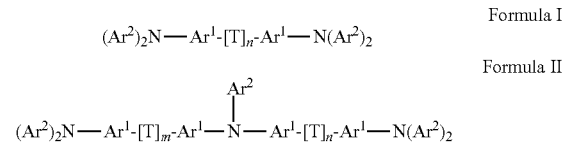

wherein:
Ar¹ is the same or different at each occurrence and is selected from the group consisting of phenylene, naphthylene, and binaphthylene;
Ar² is the same or different at each occurrence and is selected from the group consisting of phenyl, biphenyl, terphenyl, naphthyl, and binaphthyl;
m and n are the same or different and each is an integer greater than 0; and
T is the same or different at each occurrence and is a conjugated moiety including at least one triarylamino group, wherein the moiety is connected in a non-planar configuration;
wherein the compound comprises at least one set of adjacent aryl groups selected from one of the following:

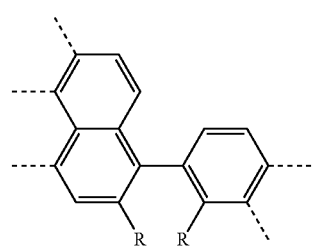

-continued

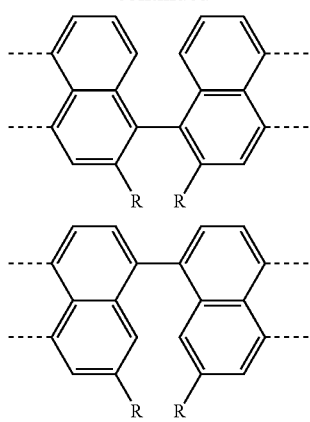

where R represents an alkyl, aryl, alkoxy, or aryloxy group and the dashed line represents a possible point of attachment.

3. An organic electronic device comprising a first electrical contact layer, a second electrical contact layer and an active layer there between, wherein the active layer comprises a liquid processable hole transport material having Formula I or Formula II:

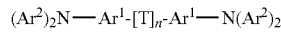

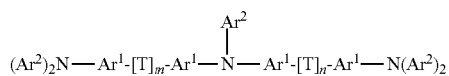

wherein:

Ar$^1$ is the same or different at each occurrence and is selected from the group consisting of phenylene, naphthylene, and binaphthylene;

Ar$^2$ is the same or different at each occurrence and is selected from the group consisting of phenyl, biphenyl, terphenyl, naphthyl, and binaphthyl;

m and n are the same or different and are an integer greater than 0; and

T is the same or different at each occurrence and is a conjugated moiety including at least one triarylamino group, wherein the moiety is connected in a non-planar configuration;

wherein the compound comprises at least one set of adjacent aryl groups selected from one of the following:

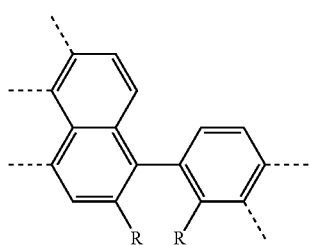

-continued

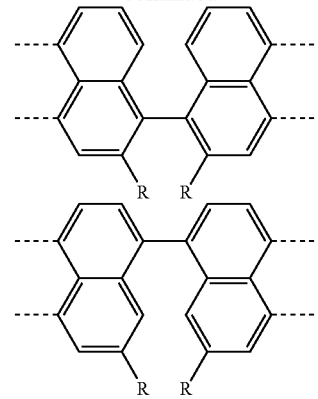

where R represents an alkyl, aryl, alkoxy, or aryloxy group and the dashed line represents a possible point of attachment.

4. The compound of claim 2, wherein T has Formula III:

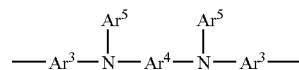

Formula III wherein:

Ar$^3$ is the same or different at each occurrence and is selected from the group consisting of phenylene, naphthylene, and binaphthylene;

Ar$^4$ is selected from the group consisting of phenylene, biphenylene, naphthylene, and binaphthylene; and Ar$^5$ is the same or different at each occurrence and is selected from the group consisting of phenyl, biphenyl, terphenyl, naphthyl, and binaphthyl.

5. The compound of claim 4, wherein Ar$^3$ has at least one substituent selected from the group consisting of alkyl and alkoxy.

6. The compound of claim 1, wherein T has Formula III:

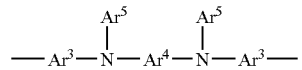

wherein:

Ar$^3$ is the same or different at each occurrence and is selected from the group consisting of phenylene, naphthylene, and binaphthylene;

Ar$^4$ is selected from the group consisting of phenylene, biphenylene, naphthylene, and binaphthylene; and Ar$^5$ is the same or different at each occurrence and is selected from the group consisting of phenyl, biphenyl, terphenyl, naphthyl, and binaphthyl.

7. The compound of claim 6, wherein Ar$^3$ has at least one substituent selected from the group consisting of alkyl and alkoxy.

8. The device of claim 3, wherein the active layer is a hole transport layer.

9. The device of claim 3, wherein the active layer is a photoactive layer and further comprises a photoactive material.

10. The device of claim 9, wherein the hole transport material functions as a host material for the photoactive material.

11. The device of claim 10, wherein the ratio of host material to photoactive material is in the range of from 5:1 to 20:1.

12. The device of claim 11, wherein the ratio of host material to photoactive material is in the range of from 10:1 to 15:1.

* * * * *